(12) United States Patent
Martín Llorens et al.

(10) Patent No.: US 10,183,127 B2
(45) Date of Patent: Jan. 22, 2019

(54) PRESSURE REDUCER FOR SUPPLYING DRUGS TO A PATIENT AND CORRESPONDING PRODUCTION METHOD

(71) Applicant: LEVENTON S.A.U., Barcelona (ES)

(72) Inventors: Jordi Martín Llorens, Barcelona (ES); Javier Torras Marí, Barcelona (ES)

(73) Assignee: LEVENTON S.A.U., Barcelona (ES)

( * ) Notice: Subject to any disclaimer, the term of this patent is extended or adjusted under 35 U.S.C. 154(b) by 478 days.

(21) Appl. No.: 14/397,598

(22) PCT Filed: May 6, 2013

(86) PCT No.: PCT/ES2013/070281
§ 371 (c)(1),
(2) Date: Oct. 28, 2014

(87) PCT Pub. No.: WO2013/167777
PCT Pub. Date: Nov. 14, 2013

(65) Prior Publication Data
US 2015/0133863 A1    May 14, 2015

(30) Foreign Application Priority Data
May 8, 2012 (ES) .................................. 201230686

(51) Int. Cl.
*A61M 5/48* (2006.01)
*A61M 5/14* (2006.01)
(Continued)

(52) U.S. Cl.
CPC ............ *A61M 5/488* (2013.01); *A61M 5/141* (2013.01); *A61M 5/16804* (2013.01);
(Continued)

(58) Field of Classification Search
CPC ........ A61M 5/488; A61M 5/141; A61M 5/48; A61M 5/16804; A61M 5/16877; A61M 2207/00; B29K 2033/12
See application file for complete search history.

(56) References Cited

U.S. PATENT DOCUMENTS

2004/0116905 A1* 6/2004 Pedersen ............... A61M 5/141
604/890.1
2006/0219624 A1* 10/2006 Kuno ..................... B01D 29/01
210/435

(Continued)

FOREIGN PATENT DOCUMENTS

WO          02/41938 A1    5/2002

*Primary Examiner* — Bhisma Mehta
*Assistant Examiner* — Hamza Darb
(74) *Attorney, Agent, or Firm* — McGlew and Tuttle, P.C.

(57) ABSTRACT

The present invention relates to a pressure reducer for delivering drugs to a patient and the corresponding method of manufacture, said pressure reducer for delivering drugs to a patient comprising: a duct (9) with an inlet (11) and an outlet (13), a first body (1) with a first surface (5), and a second body (3) with a second surface (6) directly contacting the first body (1). One of the surfaces (5,6) has a recess (7) such that a duct (9) is defined between both surfaces. Both bodies are attached to one another by means of a continuous attachment line running on both sides of the duct (9). The method of manufacture comprises a laser welding step in which the first body (1) is welded to the second body (3) by means of a welding seam extending along both sides of the duct.

20 Claims, 5 Drawing Sheets

(51) Int. Cl.
*A61M 5/168* (2006.01)
*B29C 65/16* (2006.01)
B29L 31/00 (2006.01)
B29C 65/00 (2006.01)

(52) U.S. Cl.
CPC .......... *A61M 5/16877* (2013.01); *A61M 5/48* (2013.01); *B29C 65/16* (2013.01); *A61M 2207/00* (2013.01); *B29C 65/1616* (2013.01); *B29C 65/1635* (2013.01); *B29C 65/1654* (2013.01); *B29C 66/112* (2013.01); *B29C 66/114* (2013.01); *B29C 66/244* (2013.01); *B29C 66/5346* (2013.01); *B29C 66/71* (2013.01); *B29C 66/7352* (2013.01); *B29C 66/919* (2013.01); *B29L 2031/753* (2013.01)

(56) References Cited

U.S. PATENT DOCUMENTS

2007/0065659 A1* 3/2007 Kihara .................... B29C 65/16 428/323
2011/0066108 A1* 3/2011 Geipel ................. A61M 5/141 604/151
2012/0234757 A1* 9/2012 Martin ................... A61M 5/38 210/650

* cited by examiner

FIG. 1 – State of the art

FIG. 2 – State of the art

FIG. 3 – State of the art

FIG. 4 – State of the art

FIG. 5 – State of the art

FIG. 6 – State of the art

FIG. 7 – State of the art

FIG. 8 – State of the art

PRESSURE REDUCER FOR SUPPLYING DRUGS TO A PATIENT AND CORRESPONDING PRODUCTION METHOD

FIELD OF THE INVENTION

The invention relates to a pressure reducer for delivering drugs to a patient, suitable for allowing the delivery of a certain fixed nominal flow rate of a drug, comprising: [a] a duct with an inlet and an outlet, where the duct is suitable for being traversed by the drug, [b] a first body with a first surface, and [c] a second body with a second surface, where the first body and the second body define an assembled position in which the first surface is substantially facing the second surface, and where at least one of the surfaces has at least one recess such that the duct is formed in the assembled position.

The invention also relates to a method of manufacturing a pressure reducer of the mentioned type.

STATE OF THE ART

Pressure reducers of the type mentioned above are known. In various applications where it is necessary to deliver a drug to a patient through a blood vessel, devices delivering the drug for a more or less substantial period of time, such as "dropwise" delivery under gravity, elastomeric pumps, mechanical pumps, etc., are used. These devices normally create excess pressure on the drug at the inlet of the blood vessel, for example by means of the elastic force of the balloon of an elastomeric pump, by means of the mechanical force of a mechanical pump, by means of the difference in height between the bag containing the drug and the point of entry in the blood vessel, etc. This excess pressure is normally greater than that strictly necessary for inserting the drug into the blood vessel, so these devices usually include a pressure reducer positioned at any intermediate point between the pressure-generating device and the entry in the blood vessel. These devices must generally deliver the drug at flow rates that are the most uniform possible and as close as possible to a certain nominal value.

The basic function of the pressure reducer is precisely that of reducing pressure. They usually comprise a duct which when traversed by the drug experiences a pressure loss, said pressure loss basically being a function of two parameters: the length and the cross-section of the duct. Pressure reducers are designed specifically for each type of specific application, i.e., they are designed taking into account the type of device they will be connected with and the flow rate to be delivered to the patient. For example, if a pressure reducer allowing the delivery of a certain flow rate of a drug when it is connected to an elastomeric pump is to be designed, the pressure supplied by the balloon of the elastomeric pump and the pressure losses in the entire fluid circuit must be taken into account in order to thus obtain the pressure loss that must occur in the pressure reducer to reach the desired flow rate. Given that all the components of a fluid circuit of this type are usually standardized, simply replacing one pressure reducer with another that causes a different pressure loss is sufficient to obtain a different flow rate. So it is therefore not uncommon for these pressure reducers to bear an indication with the flow rate passing through them instead of the pressure loss they generate because the flow rate is a datum to be immediately interpreted for equipment users (usually medical staff). As a result, it is also common for these pressure reducers to also be referred to as flow rate regulators, even though they are different from variable flow rate regulators, whereby it is possible with one and the same device to select a specific flow rate within a certain range.

Various types of pressure reducers, such as those formed by a glass tube with a very small internal diameter, those having a long capillary tube, etc., are known.

Document WO 0241938 discloses pressure reducers of the type mentioned above. An elastomeric joint is intercalated between the first body and the second body in such pressure reducers. This joint forms the seal and is partly deformed by being partially introduced in the duct, as described in the mentioned document WO 0241938 (for example in page 3, line 27 to page 6, line 2; page 7, line 26 to 34; page 11, line 26 to page 13, line 8; FIGS. 1 to 7). The fact that it is partially introduced in the duct means that the pressure drop is different depending on the compressive force applied on the first body and the second body when they are being attached (which is usually done by ultrasonic welding). In this sense, the hardness of the elastomeric material will also be important. This makes it necessary to introduce a system for classifying the resistance to the passage of the fluid of each pressure reducer once assembled. The hardness of the joint evolving over time (decreasing) such that it becomes further introduced in the duct as time passes also occurs. This results in the pressure loss of the pressure reducer varying overtime (increasing). This variation stops after a few weeks. The pressure drop of the pressure reducer can be reliably determined at that point, but this makes it necessary to manage intermediate product stocks that still cannot be marketed or calibrated.

SUMMARY OF THE INVENTION

The object of the invention is to overcome these drawbacks. This is achieved by means of a pressure reducer of the type mentioned above, characterized in that the second body directly contacts the first body, such that the duct is defined between the second surface and the first surface, and in that the first body and the second body are attached to one another by means of at least one continuous attachment line running on both sides of the duct from the inlet to the outlet. The second body, which is a rigid part, does indeed directly close the duct in a leak-tight manner. This allows eliminating any type of intermediate joint, and since the duct is defined directly by two rigid bodies (the first body and the second body) the pressure reducer does not experience all the problems described above, so it relates to the variations in the values of the pressure drop that the fluid will experience as is traverses the duct. This continuous attachment line is preferably a weld advantageously formed by a laser. The laser allowed easily forming welding seams that are long and have complex geometries, which allows forming the required continuous attachment line.

The pressure reducers of the type mentioned above can have various shapes, although they are preferably substantially planar. In this case, the duct is normally a channel arranged on the first surface of the first body (although it can also be partially complemented with a channel arranged on the second surface of the second body). In this case, the pressure reducer according to the invention has two continuous attachment lines, one on each side of the duct and extending from the inlet to the outlet.

The second body is preferably made of a material that is transparent at a pre-established wavelength, and the first body advantageously absorbs this pre-established wavelength. This does indeed allow laser welding, such that the laser beam traverses the second body and is absorbed in the first surface of the first body, such that a molten region is formed which will generate the welding seam defining the continuous attachment line. Any laser having suitable power and precision can generally be used, but it is particularly advantageous to use a laser with ytterbium (Yb) crystal. The pre-established wavelength is preferably 1070 nm (nanometers) or 1064 nm.

The second body is advantageously made of poly(methyl methacrylate) (PMMA). This material is transparent at the preferred wavelengths mentioned above. In turn, it is advantageous for the first body to be made of methyl methacrylate-acrylonitrile-butadiene-styrene (MABS). As previously stated, it is advantageous for the first body to absorb a pre-established wavelength to thus be able to form the laser weld. To that end, the first body can be made from a material that absorbs the mentioned wavelength or it can be made of any other material (that is transparent at the mentioned wavelength) and include an additive that absorbs the wavelength in question.

The second body is preferably a sheet with a smooth second surface, and it advantageously has a thickness comprised between 20 microns and 500 microns. It is particularly advantageous for it to have a thickness between 40 microns and 200 microns. The second body can indeed be obtained in that form by die cutting a prefabricated sheet, making it easy and less expensive to obtain. With these thicknesses, the second body is already rigid enough to perform its function and allows suitable laser welding. In the event that the second body is a sheet like that mentioned, it is advantageous to subsequently assemble a cover for protecting the sheet on the already welded sheet. Another alternative could be to directly assemble a thicker second body, preferably comprised between 0.5 mm and 2 mm, in which case it is no longer advisable to add a cover.

Another object of the invention is a method of manufacturing a pressure reducer according to the invention, characterized in that it comprises a laser welding step in which the first body is welded to the second body by means of at least one welding seam extending along both sides of the duct from the inlet to the outlet.

The welding step is advantageously performed with a laser with ytterbium crystal, preferably a continuous-wave fiber laser. The laser can be the IPG YLM-20-SC® continuous-wave fiber laser having a maximum power of 20 W, with a TWIST® head developed by the company ILT Fraunhofer, for example. This laser has a focal length of 100 mm to 254 mm and a focus diameter between 40 microns and 75 microns.

The method advantageously comprises a step in which a cover is fixed at least partially covering the second body. Alternatively, as mentioned above, a thicker second body can be used such that it is no longer advisable to add a cover.

BRIEF DESCRIPTION OF THE DRAWINGS

Other advantages and features of the invention can be seen from the following description in which a preferred embodiment/preferred embodiments of the invention is/are described in a non-limiting manner in reference to the attached drawings. In the drawings.

DETAILED DESCRIPTION OF SEVERAL EMBODIMENTS OF THE INVENTION

Figure 1:
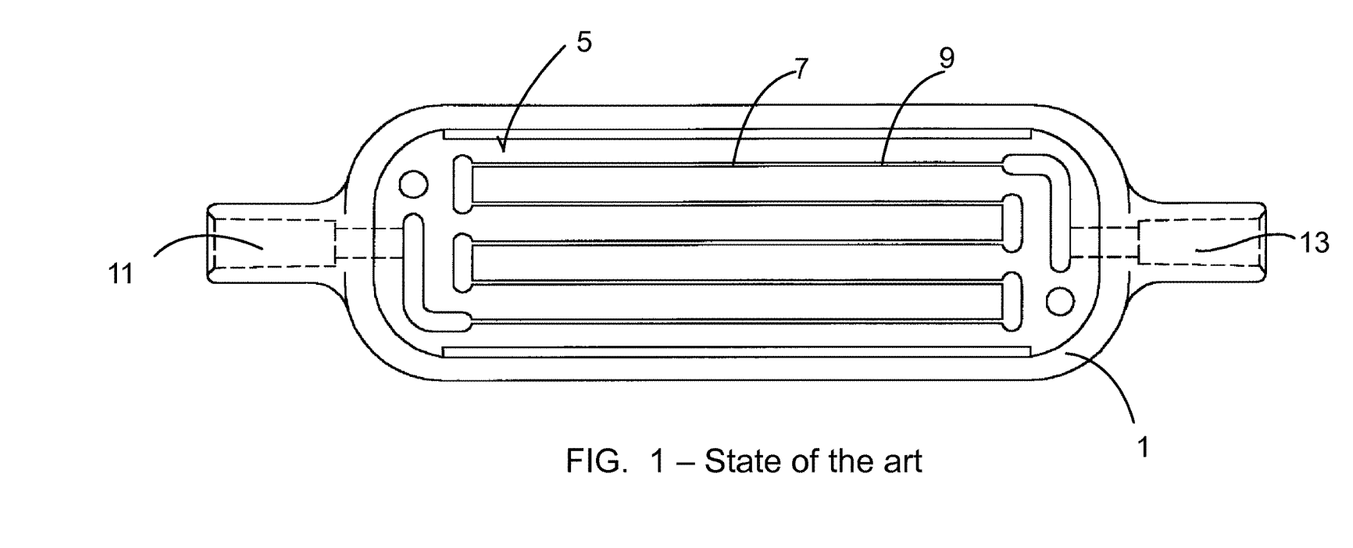
FIGS. 1 to 3 show plan, partially sectioned elevational and perspective views of a first body of a pressure reducer according to the state of the art.
Figure 2:
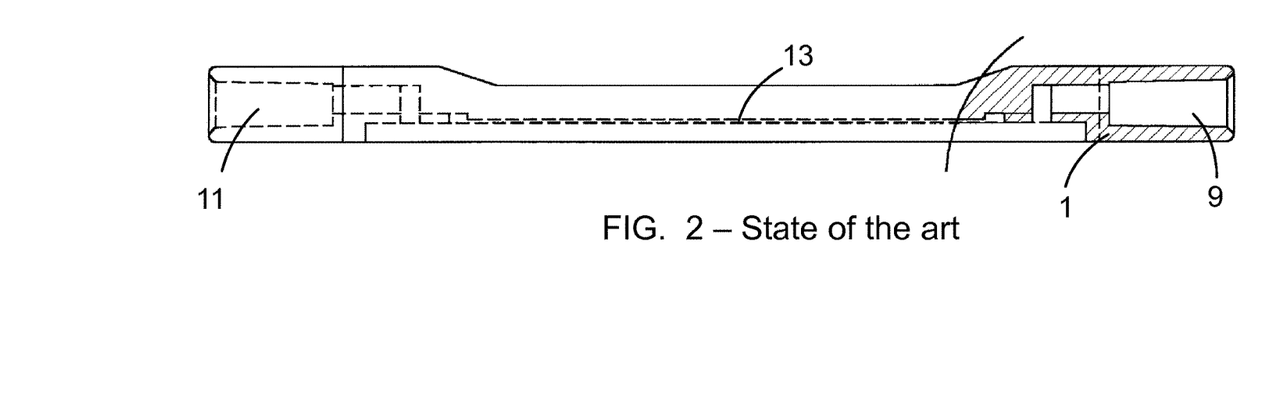
Figure 3:
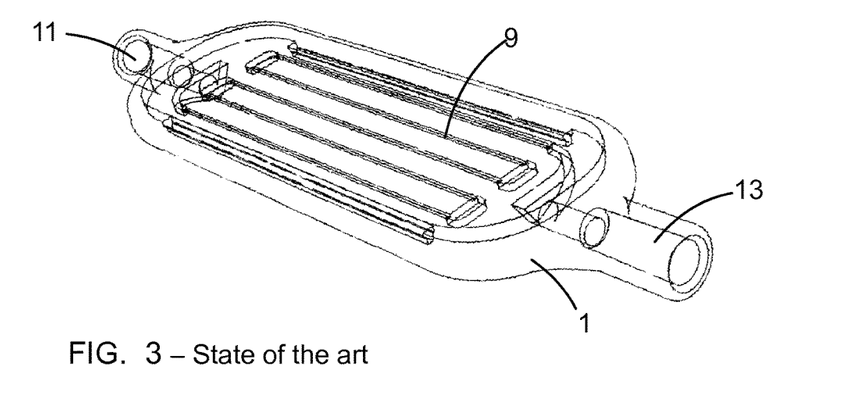
Figure 4:
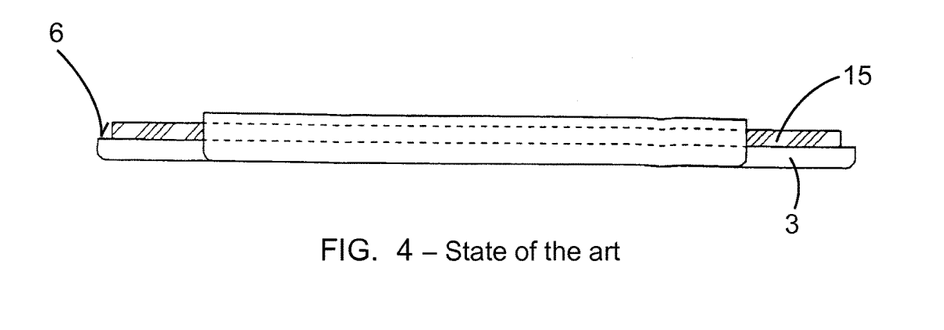
FIGS. 4 and 5 show elevational and plan views of a second body with a joint of a pressure reducer according to the state of the art.
Figure 5:
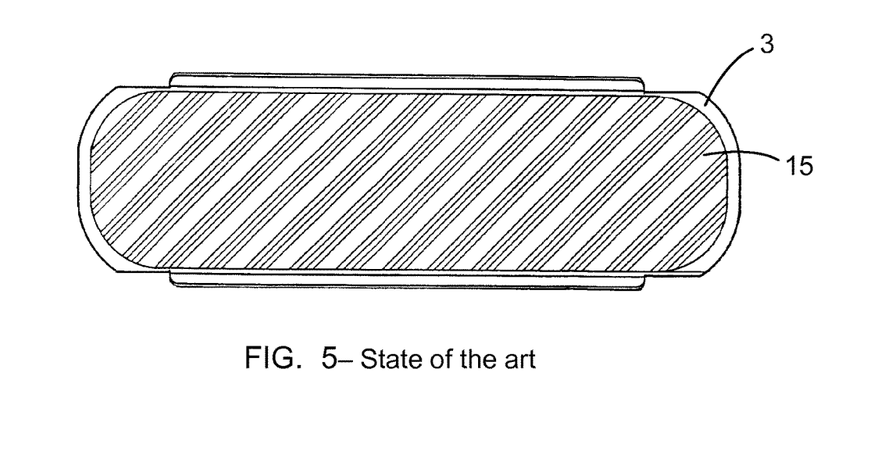
Figure 6:
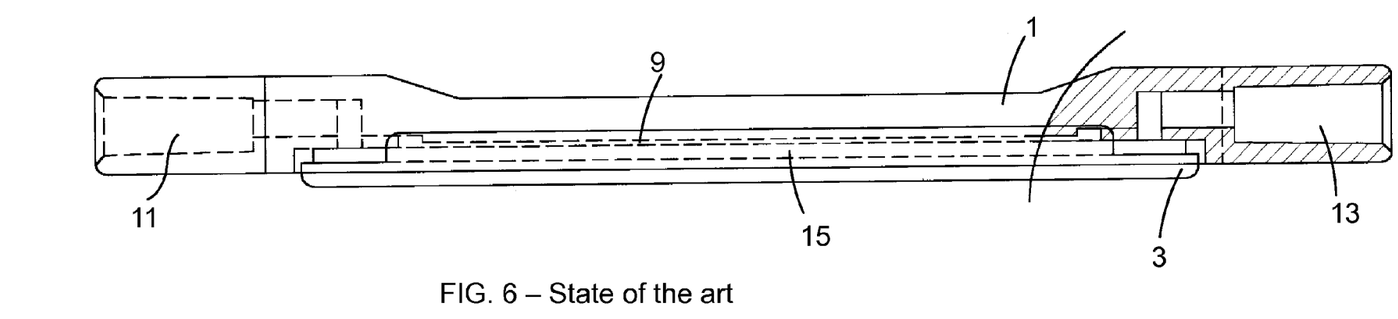
FIG. 6 shows a partially sectioned elevational view of the first body of FIG. 1 and the second body of FIG. 4 assembled with one another.
Figure 7:
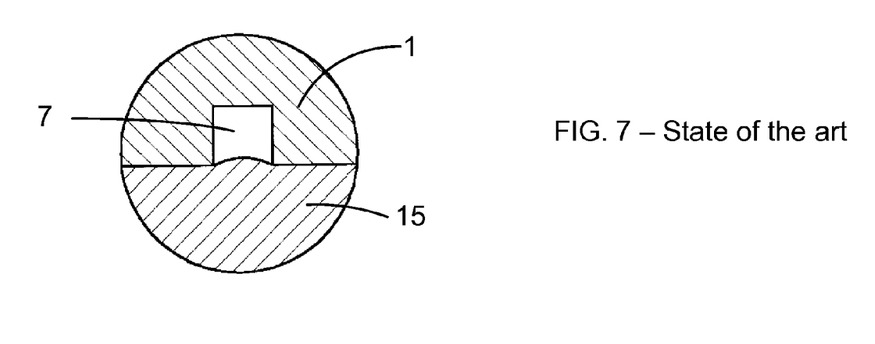
FIG. 7 shows a view of a detail of a recess of the first body with the joint partially introduced.

FIGS. 1 to 5 show a first body 1 and a second body 3 of a pressure reducer according to the state of the art, specifically as described in document WO 0241938, page 11, line 26 to page 13, line 8; FIGS. 1 to 7. The first body 1 has a first surface 5 in which there is a groove or recess 7 that will form the duct 9 extending from an inlet 11 to an outlet 13. The second body 3 in turn has a joint 15 injected on to a second surface 6. FIG. 6 shows both the first body 1 and the second body 3 assembled with one another, with the joint 15 forming the leak-tight closure. When the second body 3 is assembled on the first body 1, the joint 15 is partially introduced in the groove or recess 7, as shown in FIG. 7.

Figure 8:
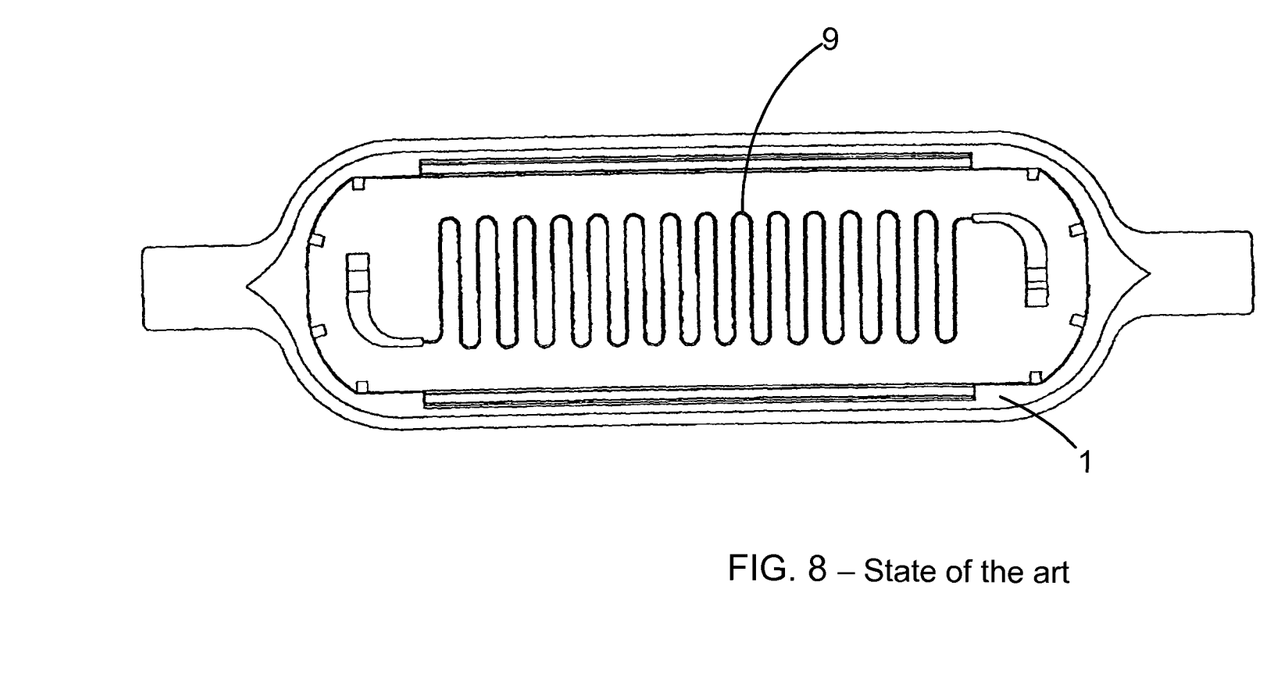
FIG. 8 shows a plan view of another first body according to the state of the art.

FIG. 8 shows another first body 1 of a pressure reducer according to the state of the art with a different geometric arrangement of the duct 9.

Figure 9:
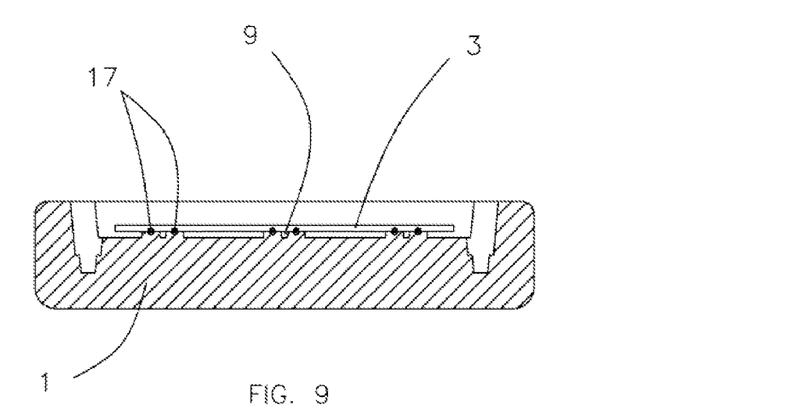
FIG. 9 shows a cross-section view of a pressure reducer according to the invention.

FIG. 9 shows a cross-section view of a pressure reducer according to the invention. The pressure reducer comprises a first body 1 which generally is substantially identical to the first body of the pressure reducers according to the state of the art. The difference is in the second body 3, which is attached directly to the first body 1 without there being any additional element between them. The second body 3 is attached to the first body 1 by means of a welding seam 17 running on both sides of the duct 9 from the inlet 11 to the outlet 13.

Figure 10:
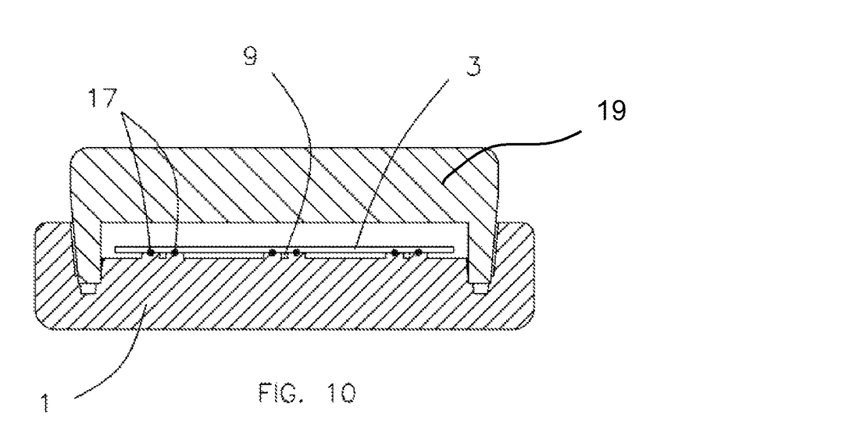
FIG. 10 shows a cross-section view of the pressure reducer of FIG. 9 with a cover.

FIG. 10 shows a cross-section view of another pressure reducer according to the invention. This pressure reducer is in theory the same as the pressure reducer of FIG. 9, but it includes a cover 19 covering the second body 3. This cover 19 does not participate in defining the duct 9 or in the leak-tight closure thereof, but rather it is a protection for the second body 3.

Figure 11:
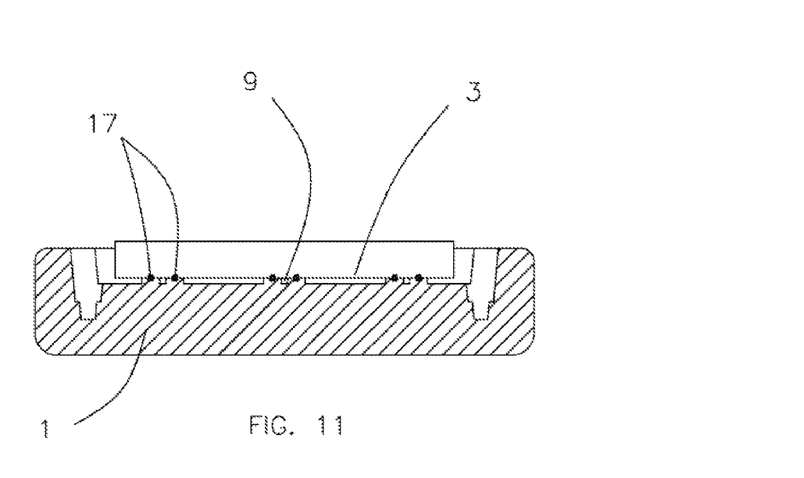
FIG. 11 shows a cross-section view of another pressure reducer according to the invention.

FIG. 11 shows another pressure reducer according to the invention. In this case the second body 3 is thicker, making it more rigid and robust so it is no longer advisable to include a protective cover.

The invention claimed is:

1. A substantially planar pressure reducer for delivering drugs to a patient, suitable for allowing the delivery of a certain fixed nominal flow rate of a drug, the pressure reducer comprising:
    a duct with an inlet and an outlet, said duct being suitable for being traversed by said drug, and said duct defining only a single flow path for transferring the drug in a fluid flow direction from said inlet to said outlet;
    a first body comprising at least two projections, the at least two projections having top surfaces; and
    a second body, said first body and said second body being impermeable, wherein said first body and said second body define an assembled position in which said first body is fixed to said at least two projections such that said second body is positioned on and attached to said at least two projections without said second body contacting a remaining portion of said first body, said at least two projections forming boundaries of the flow path, said at least two projections defining at least one recess such that said duct is formed in said assembled position.

2. The pressure reducer according to claim 1, wherein said second body is a sheet with a smooth surface, wherein no structure is provided between said first body and said second body and no structure is provided in said duct.

3. The pressure reducer according to claim 2, wherein said second body has a thickness comprised between 20 microns and 500 microns.

4. The pressure reducer according to claim 2, wherein said second body has a thickness comprised between 0.5 mm and 2 mm.

5. The pressure reducer according to claim 4, wherein said second body is made of a material that is transparent at a pre-established wavelength, a first weld seam and a second weld seam extending exclusively in an axial direction of the duct.

6. The pressure reducer according to claim 2, wherein said second body has a thickness comprised between 40 microns and 200 microns.

7. The pressure reducer according to claim 1, further comprising:
a cover, said cover at least partially covering said second body.

8. The pressure reducer according to claim 1, further comprising:
a cover, said cover being in direct contact with said first body, said cover being located at a spaced location from said second body.

9. The pressure reducer according to claim 8, wherein at least said cover defines an interior space, said second body being arranged completely in said interior space.

10. The pressure reducer according to claim 1, wherein the first body is fixed to the second body via at least one continuous attachment line, wherein said at least one continuous attachment line is provided between one of the top surfaces of one of the projections and a first area of the second body and between another one of the top surfaces of one of the projections and a second area of the second body, wherein said first area is arranged on one of the sides of the duct and said second area is arranged on another one of the sides of the duct.

11. The pressure reducer according to claim 10, wherein said top surfaces are parallel to the substantially planar reducer.

12. The pressure reducer according to claim 1, wherein said first body is fixed to said second body via at least one continuous attachment line extending along a first side of said duct and along a second side of said duct, said first side being located opposite said second side in a direction traversing said fluid flow direction, wherein said at least one continuous attachment line is a continuous attachment line formed by one of a continuous welding line, a continuous heat sealing line and a continuous bonding line.

13. A method of manufacturing a substantially planar pressure reducer, the method comprising:
providing a duct with an inlet and an outlet, said duct being suitable for being traversed by a drug, and said duct defining only a single flow path for transferring the drug in a fluid flow direction from said inlet to said outlet;
providing a first body comprising at least two projections forming boundaries of said single flow path;
providing a second body with a surface, said surface being substantially planar and parallel to the substantially planar pressure reducer, wherein said first body and said second body are impermeable and define an assembled position such that said duct is defined between said second body and said first body;
attaching said first body to said second body such that said second body is positioned on and attached to top surfaces of said at least two projections without said second body contacting a remaining portion of said first body.

14. The method according to claim 13, further comprising:
providing a cover, said cover being fixed at least partially covering said second body, wherein each of said top surfaces is in direct contact with a portion of said surface of said second body, wherein no structure is provided between said first body and said second body and no structure is provided in said duct.

15. The method according to claim 13, wherein said at least two projections maintain said second body at a spaced location from said remaining portion of said first body, wherein a first welding seam is provided between one of the at least two projections and a first area of the second body, and a second welding seam is provided between another one of the at least two projections and a second area of the second body, wherein the first area is arranged on one of the sides of the duct and the second area is arranged on another one of the sides of the duct, the first weld seam and the second weld seam extending exclusively in an axial direction of the first body and the second body.

16. The method according to claim 13, further comprising:
providing a cover, said cover being in direct contact with said first body, said cover being located at a spaced location from said second body, wherein said first body is fixed to said second body via at least one continuous attachment line extending along a first side of said duct and along a second side of said duct, said first side being located opposite said second side in a direction traversing said fluid flow direction, wherein said at least one continuous attachment line is a continuous attachment line formed by one of a continuous welding line, a continuous heat sealing line and a continuous bonding line.

17. The method according to claim 13, wherein at least said cover defines an interior space, said second body being arranged completely in said interior space.

18. A pressure reducer for delivering drugs to a patient, suitable for allowing the delivery of a certain fixed nominal flow rate of a drug, the pressure reducer comprising:
a first body comprising a base body and at least two projections having top surfaces; and
a second body, said first body and said second body being impermeable to fluid, said at least two projections defining at least a portion of a duct comprising an inlet and an outlet, wherein the duct defines only a single flow path for transferring the drug in a fluid flow direction from said inlet to said outlet, said at least two projections defining boundaries of said single flow path, at least a portion of said second body being in direct contact with said first body, said second body being fixed to said top surfaces of said at least two projections such that said at least two projections maintain said second body at a spaced location from said base body, wherein said second body is free from contact with said base body.

19. The pressure reducer according to claim 18, further comprising:
a cover, said cover being in direct contact with said first body, said second body being fixed to said first body via at least a first continuous connection seam and at least a second continuous connection seam, said first continuous connection seam extending along a first side of said duct, said second continuous connection seam extending along a second side of said duct, said first continuous connection seam and said second continuous connection seam comprising one or more of welded material, material of said first body and material of said second body.

20. The pressure reducer according to claim 19, wherein said cover is located at a spaced location from said second body, said top surfaces being parallel to a longitudinal axis of said first body.

\* \* \* \* \*